United States Patent [19]

Blaser et al.

[11] 4,335,055

[45] Jun. 15, 1982

[54] PROCESS FOR THE PREPARATION OF ALKENYLBENZENE DERIVATIVES OR ALKENYLNAPHTHALENE DERIVATIVES

[75] Inventors: Hans-Ulrich Blaser, Ettingen, Switzerland; Dieter Reinehr, Kandern, Fed. Rep. of Germany; Alwyn Spencer, Basel, Switzerland

[73] Assignee: Ciba-Geigy Corporation, Ardsley, N.Y.

[21] Appl. No.: 262,002

[22] Filed: May 8, 1981

[30] Foreign Application Priority Data

May 13, 1980 [CH] Switzerland .......................... 3731/80

[51] Int. Cl.³ .................... C07C 121/70; C07C 15/52; C07C 25/24; C07C 49/217

[52] U.S. Cl. ................................ 260/465 K; 570/184; 570/200; 260/465 D; 585/436; 585/437; 260/465 E; 549/370; 549/448; 260/465 F; 544/301; 564/305; 260/465 G; 564/428; 568/30; 260/465 H; 568/31; 568/33; 560/8; 568/34; 568/306; 560/10; 568/316; 568/424; 560/11; 568/433; 568/592; 560/19; 568/631; 568/632; 560/20; 568/633; 568/634; 560/21; 568/635; 568/636; 560/51; 568/637; 568/639; 560/52; 568/640; 568/642; 560/55; 568/643; 560/56; 560/80; 560/81; 560/96; 560/100; 560/101; 560/102; 560/138; 560/139; 568/646; 568/647; 568/928; 568/929; 568/930; 568/931; 570/128; 570/143; 570/183

[58] Field of Search .......... 260/465 D, 465 H, 465 K; 560/8; 568/433, 631, 646, 928; 570/183, 184, 200; 585/436, 437

[56] References Cited

U.S. PATENT DOCUMENTS 3,922,299 11/1975 Heck ..................................... 560/104

4,108,887 8/1978 Fleck et al. ..................... 260/465 H

FOREIGN PATENT DOCUMENTS 1445231 8/1976 United Kingdom .

OTHER PUBLICATIONS

Tohda et al., Synthesis, Nov. 1977, pp. 777-778 (1977).
Chiusoli et al., Transition Metal Chemistry, vol. 2, pp. 270-272 (1977).
Biavati et al., Transition Metal Chemistry, vol. 4, pp. 398-399 (1979).

*Primary Examiner*—Dolph H. Torrence
*Attorney, Agent, or Firm*—Michael W. Glynn

[57] ABSTRACT

Compounds of the formula I

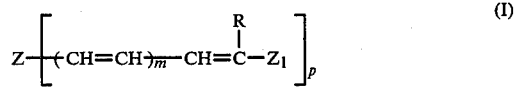

(I)

in which Z, $Z_1$, R, m and p are as defined in patent claim 1, can be obtained in a simple and economical manner by a novel process wherein a halide of the formula II

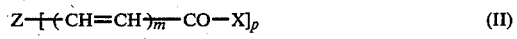

(II)

is reacted with a substituted or unsubstituted vinylbenzene or vinylnaphthalene derivative in the presence of a base and of certain palladium catalysts, such as palladium acetate. The compounds (I) or functional derivatives preparable therefrom are useful, for example, for the preparation of known dyes or fluorescent brighteners, or can be used directly as fluorescent brighteners or as scintillators.

13 Claims, No Drawings

PROCESS FOR THE PREPARATION OF ALKENYLBENZENE DERIVATIVES OR ALKENYLNAPHTHALENE DERIVATIVES

The present invention relates to a novel process for the preparation of alkenylbenzene derivatives or alkenylnaphthalene derivatives.

U.S. Pat. No. 3,922,299 discloses that vinyl-substituted or allyl-substituted organic compounds, especially cinnamic acid and cinnamic acid esters, can be prepared by catalytic reaction of the corresponding halides with activated olefins, such as methyl acrylate, in the presence of tertiary amines. The preferred catalysts used are mixtures of palladium acetate and triphenylphosphine or tri-(ortho-tolyl)-phosphine. The reaction can also be carried out by first forming a complex of the halide with the catalyst system and then allowing this to react with the olefin in the presence of a tertiary amine. On the other hand it is known that the reaction of benzoyl chloride with methyl acrylate in the presence of stoichiometric amounts of a nickel(O) catalyst results, on after-treatment of the reaction mixture with iodine in methanol, in the formation of trans-(methyl 3-benzoylacrylate). At the same time, methyl cinnamate is formed as a by-product. Reaction of a complex of benzoyl-palladium chloride and triphenylphosphine with methyl acrylate at 70°–85° C. in the presence of triethylamine gives methyl cinnamate as the main product and methyl benzoylacrylate as a by-product. If the palladium and triphenylphosphine are employed only in catalytic amounts, the reaction equilibrium shifts in favour of the formation of methyl benzoylacrylate (weight ratio of methyl benzoylacrylate to methyl cinnamate=about 8.3 :)[cf. Transition Met. Chem. 2, 270 (1977) and 4, 398 (1979)]. Finally, it is known from Synthesis, 777 (1977) that the reaction of aromatic acid halides with 1-alkynes, catalysed by Pd, gives alkynyl ketones, without decarbonylation occurring.

It has now been found that compounds of the formula I

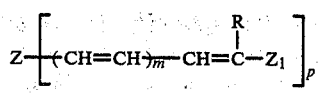

in which, if p=1, Z is substituted or unsubstituted phenyl or naphthyl and, if p=2, Z is substituted or unsubstituted phenylene, naphthylene or p-biphenylene, $Z_1$ is substituted or unsubstituted phenyl or naphthyl, R is hydrogen or $C_{1-4}$-alykyl, m is zero or 1 and p is 1 or 2, can be prepared by a process wherein a compound of the formula II

in which Z, m and p are as defined under formula I and X is chlorine, bromine or iodine, is reacted, in the presence of a base and with the addition, as a catalyst, of palladium metal or of a palladium compound which under the reaction conditions forms a phosphorus-free labile palladium(O) compound, with a compound of the formula III or, if p=2, alternatively with a mixture of two different compounds of the formula III

in which R and $Z_1$ are as defined under formula I.

Using the process according to the invention, the compounds of the formula I can be prepared in a simple, economical manner and using easily accessible starting materials. It is surprising that the reaction takes place selectively, with decarbonylation of the acid halides of the formula II.

The substituents present in groups Z and $Z_1$ are inert under the reaction conditions. The said groups Z and $Z_1$ can be monosubstituted or polysubstituted, and in the latter case the substituents can be identical or different.

Examples of suitable substituents on group Z or $Z_1$ are halogen atoms and formyl, $—CH(OCH_3)_2$, $—CH(OC_2H_5)_2$,

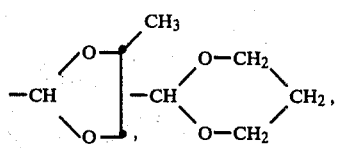

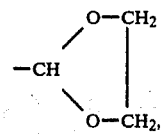

$—CH=CH—CN$, $—CH=CH—COO—C_{1-4}$-alkyl, $C_{1-10}$-alkyl, $C_{1-16}$-alkoxy, phenoxy, di-($C_{1-10}$-alkyl)-amino, nitro, cyano, $—CH_2Cl$, trifluoromethyl, benzyl, $C_{1-4}$-alkylsulfonyl, $—CO—C_{1-10}$-alkyl, $—CO$-phenyl,

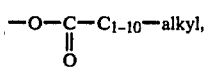

$—COO—C_{1-10}$-alkyl, $—COO$-phenyl, phenyl or naphthyl groups, which in turn can be substituted by halogen atoms or $C_{1-10}$-alkyl, $C_{1-10}$-alkoxy, di-($C_{1-10}$-alkyl)-amino, nitro, cyano, trifluoromethyl, $—CO—C_{1-10}$-alkyl, $—CO$-phenyl, $—COO—C_{1-10}$-alkyl or $—COO$-phenyl groups. Phenyl and naphthyl substituents on group Z or $Z_1$ are preferably monosubstituted or unsubstituted. Alkyl groups R, and alkyl and alkoxy groups in the abovementioned substituents can be straight-chain or branched, and alkyl and alkoxy substituents on group Z or $Z_1$ preferably have 1 to 8 and especially 1 to 4 C atoms. Examples of halogen substituents are fluorine, chlorine and bromine. Examples of groups R, or substituents on groups Z or $Z_1$, which accord with the above definitions are the methyl, ethyl, n-propyl, isopropyl, n-, sec.- and tert.-butyl, n-pentyl, 2-pentyl, n-hexyl, n-heptyl, n-octyl and n-decyl groups; the methoxy, ethoxy, n-propoxy, n-butoxy, n-hexyloxy and n-decyloxy groups; the N,N-dimethylamino, N,N-diethylamino, N,N-di-n-propylamino, N,N-di-n-butylamino, N,N-di-n-hexylamino, N,N-di-n-octylamino, N-methyl-N-ethylamino, N-methyl-N-n-propylamino, N-ethyl-N-n-hexylamino and N-ethyl-N-n-butylamino groups; the methysulfonyl and ethylsulfonyl groups; the acetyl, propionyl, butyryl, valeroyl and octanoyl groups; the carboxylic acid methyl ester, ethyl ester, n-propyl ester, isopropyl ester, n-butyl ester, n-pentyl ester, n-hexyl ester, n-heptyl ester and n-decyl ester groups; —CH=CHCOOCH$_3$ and —CH=CHCOOC$_2$H$_5$.

Alkyl groups R preferably have a straight chain and one or two C atoms. X in formula II is preferably chlorine.

Suitable compounds of the formulae II and III are in particular:

1. Compounds of the formulae IIa and IIIa

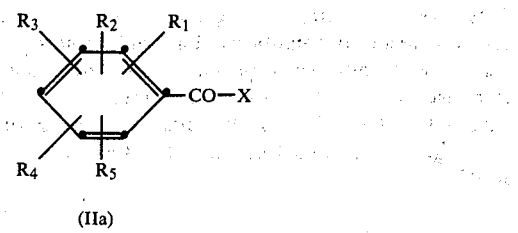

(IIa)

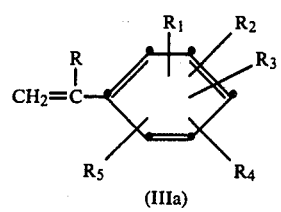

(IIIa)

in which X is chlorine or bromine, R is methyl and especially hydrogen, R$_1$ is hydrogen, Cl, Br, F, I, formyl, —CH(OCH$_3$)$_2$, —CH(OC$_2$H$_5$)$_2$,

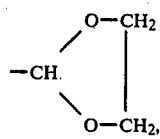

—CH=CH—CN, —CH=CHCOOCH$_3$, —CH=CH-COOC$_2$H$_5$, C$_{1-4}$-alkyl, C$_{1-4}$alkoxy, phenoxy, di-(C$_{1-2}$-alkyl)-amino, —NO$_2$, —CN, —CF$_3$, C$_{1-4}$-alkylsulfonyl, benzyl, —CO—C$_{1-4}$-alkyl, —CO-phenyl, —OCO—C$_{1-4}$-alkyl, —COO—C$_{1-4}$alkyl, —COO-phenyl, phenyl, chlorophenyl, bromophenyl, methylphenyl, methoxyphenyl, 1-naphthyl or 2-naphthyl, R$_2$ and R$_3$ independently of one another are hydrogen, Cl, Br, F, —NO$_2$, C$_{1-4}$-alkyl or C$_{1-4}$-alkoxy, especially methyl or methoxy, and R$_4$ and R$_5$ are hydrogen or, if R$_1$, R$_2$ and R$_3$ are each chlorine, bromine, fluorine or methyl, are also each chlorine, bromine, fluorine or methyl. Preferred compounds are those of the formula IIIa, and especially those of the formula IIa, in which X is chlorine, R is methyl and especially hydrogen, R$_1$ is hydrogen, Cl, Br, F, I, —CH=CHCN, —CH=CHCOOCH$_3$, —CH=CHCOOC$_2$H$_5$, C$_{1-4}$-alkyl, especially methyl or ethyl, methoxy, N,N-dimethylamino, —NO$_2$, —CN, formyl, methylsulfonyl or phenyl, R$_2$ is hydrogen, Cl, Br, methyl, ethyl, methoxy or nitro, R$_3$ is hydrogen, Cl, Br, methyl, ethyl or methoxy and R$_4$ and R$_5$ are each hydrogen.

2. Compounds of the formula IIb

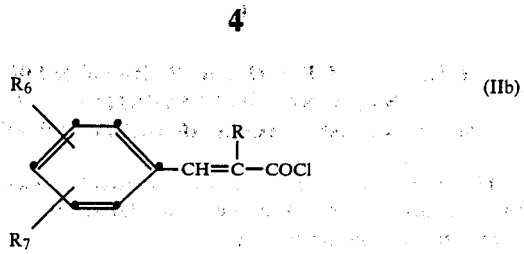

in which R is methyl or, especially, hydrogen, R$_6$ is hydrogen, Cl, Br, F, —NO$_2$, —CN, —SO$_2$CH$_3$, methyl, ethyl, methoxy, ethoxy, —CHO or —CH(OCH$_3$)$_2$ and R$_7$ is hydrogen, Cl, Br, F, —NO$_2$, methyl, ethyl, methoxy or ethoxy. Preferred compounds of the formula IIb are those in which R is methyl or, especially, hydrogen, R$_6$ is hydrogen, methyl, methoxy, Cl, Br, F, —NO$_2$ or —CHO and R$_7$ is hydrogen.

3. Compounds of the formula IIc

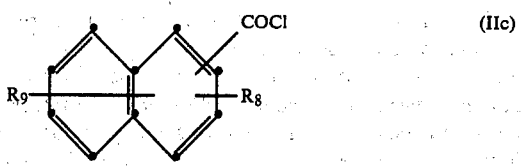

in which the group —COCl is in the 1- or 2-position, R$_8$ and R$_9$ can be bonded to one and the same ring or to different rings, R$_8$ is hydrogen, Cl, Br, F, methyl, ethyl, methoxy, ethoxy, —CHO, —COCH$_3$, —SO$_2$CH$_3$, —CN, —NO$_2$ or —CH(OCH$_3$)$_2$ and R$_9$ is hydrogen, Cl, Br, F, methyl, methoxy or —NO$_2$. Preferred compounds of the formula IIc are those in which R$_8$ is methyl or, especially, hydrogen and R$_9$ is hydrogen.

4. Compounds of the formula IId

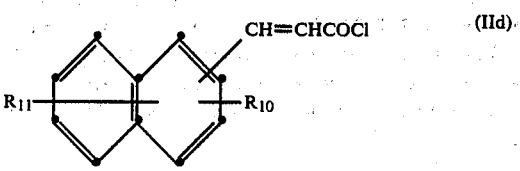

in which the group —CH=CHCOCl is bonded to the 1- or 2-position, R$_{10}$ and R$_{11}$ can be bonded to one and the same ring or to different rings, R$_{10}$ is hydrogen, Cl, Br, F, methyl, methoxy, —NO$_2$, —CHO, —CN, —SO$_2$CH$_3$ or —CH(OCH$_3$)$_2$ and R$_{11}$ is hydrogen, Cl, Br, F, methyl, methoxy or —NO$_2$. Preferred compounds of the formula IId are those in which R$_{10}$ is hydrogen or methyl and R$_{11}$ is hydrogen.

5. Compounds of the formula IIe

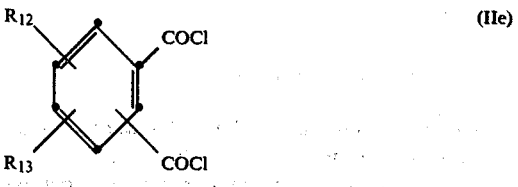

in which R$_{12}$ is hydrogen, —CO-phenyl, Cl, Br, F, —CN, —CHO, —NO$_2$ or methyl and R$_{13}$ is hydrogen, Cl, Br, F or methyl. Preferred compounds of the formula IIe are isophthalic acid dichloride and terephthalic acid dichloride, which are unsubstituted or substituted by a methyl or NO₂ group, the unsubstituted compounds being especially preferred.

6. Compounds of the formula IIf

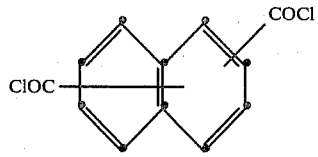

(IIf)

in which the —COCl groups can be bonded to one and the same ring or to different rings. Preferred compounds of the formula IIf are 1,4- and 2,6-naphthalenedicarboxylic acid dichloride.

7. Compounds of the formula IIg

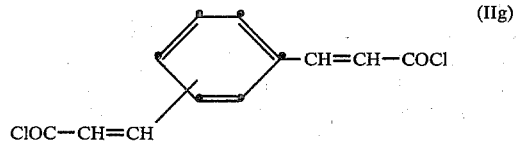

(IIg)

in which the —CH=CH—COCl groups are preferably in the 1,3- or 1,4-position.

8. Compounds of the formula IIh

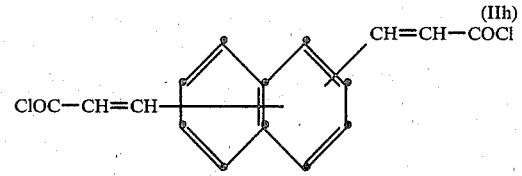

(IIh)

in which the —CH=CH—COCl groups are bonded to one and the same ring or to different rings and are preferably in the 1,4- or 2,6-position.

9. The compound of the formula IIi

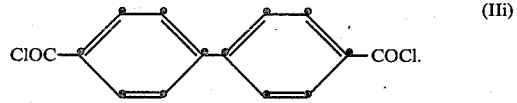

(IIi)

R is preferably methyl or, especially, hydrogen. Preferred compounds of the formula I, with p=2, are symmetrical compounds, i.e. those in which R and $Z_1$ have the same meaning in each of the two groups —CH=C(R)—$Z_1$.

Particularly preferred acid halides are compounds of the formula IIa, in which X is chlorine, $R_1$ is hydrogen, formyl, methyl, methoxy, cyano, nitro, Cl, Br, F, I, —CH=CHCN, —CH=CHCOOCH₃, —CH=CH-COOC₂H₅ or phenyl, $R_2$ is hydrogen, methyl, methoxy, Cl or Br, $R_3$ is hydrogen or methoxy and $R_4$ and $R_5$ are each hydrogen; compounds of the formula IIb, in which R is methyl or, especially, hydrogen, $R_6$ is hydrogen, Cl or nitro and $R_7$ is hydrogen; compounds of the formula IIc, in which $R_8$ is methyl or, especially, hydrogen and $R_9$ in hydrogen; unsubstituted isophthalic acid dichloride and terephthalic acid dichloride; 1,4- and 2,6-naphthalenedicarboxylic acid dichloride; and compounds of the formula IIg, in which the —CH=CH—COCl groups are in the 1,3-position or 1,4-position, as well as 4,4'-diphenyldicarboxylic acid dichloride. The use of 4-bromobenzoyl chloride or of benzoyl chloride is particularly preferred.

Preferred compounds of the formula III are those in which R is methyl or, especially, hydrogen, and $Z_1$ is chlorophenyl, bromophenyl, cinnamonitrile, methylphenyl, methoxyphenyl, naphthyl or, especially, phenyl. 4-Bromostyrene and styrene are the most preferred compounds of the formula III.

The catalysts, and the compounds of the formulae II and III, are known or can be prepared by methods known per se. With regard to the preparation of compounds of the formula II, reference may be made, for example, to "Organikum", 387–388, VEB Deutscher Verlag der Wissenschaften, Berlin 1964. The compounds of the formula III are employed in not less than the stoichiometric amount. Preferably, an excess of the compounds of the formula III, for example up to about 1.5 mols of the compound of the formula III per acid halide group, is used.

The palladium compounds according to the definition, which can be used as an alternative to palladium metal, are, for example, compounds of the formula IV $$M^y[PdL_n]^x \qquad (IV)$$

in which n is an integer from 2 to 4, x is 2+ to 2−, y=−(x), M, if x is not O, is a counter-ion, and the L's are identical or different phosphorus-free ligands, for example Cl, Br, I, —CN, —NO₃, $C_{1-12}$alkyl-COO,

NH₃, 2,2'-bipyridyl, o-phenanthroline,

or —NC-phenyl. Examples of suitable compounds of the formula IV are PdCl₂, PdBr₂, Pd(CN)₂, Pd(NO₃)₂, Pd(O₂C—$C_{1-12}$-alkyl)₂, especially Pd(OOCCH₃)₂,

[Pd(NH₃)₄]Cl₂, [PdCl₄]Na₂, Pd(OOCCH₃)₂(2,2'-bipyridyl), Pd(OOCCH₃)₂-(o-phenanthroline),

and PdCl₂(NC-phenyl)₂.

In addition to the above compounds, palladium compounds of other oxidation levels can also be employed, for example bis-(dibenzylidene-acetone)-palladium(O) and bis-(isonitrile)-palladium(O) compounds. Examples of the latter are bis-(cyclohexylisonitrile)-palladium(O), bis-(isopropylisonitrile)-palladium(O), bis-(tert.-butylisonitrile)-palladium(O), bis-(p-tolylisonitrile)-palladium(O), bis-(phenylisonitrile)-palladium(O) and bis-(p-methoxyphenylisonitrile)-palladium(O). Amongst these, bis-(dibenzylidene-acetone)-palladium(O), bis-(cyclohexylisonitrile)-palladium(O) and bis-(isopropylisonitrile)-palladium(O) are preferred.

The preferred catalysts are PdCl$_2$, PdBr$_2$, Pd(OOCCH$_3$)$_2$,

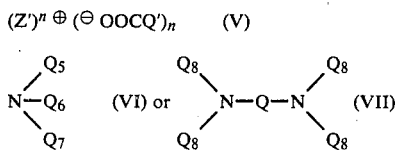

Pd(OOCCH$_3$)$_2$(2,2'-bipyridyl), PdCl$_2$(NC-phenyl)$_2$, bis-(dibenzylidene-acetone)-palladium(O) and bis-(cyclohexylisonitrile)-palladium(O). The most preferred catalysts are PdCl$_2$, palladium acetate and bis-(dibenzylidene-acetone)-palladium(O).

The catalysts are in general employed in an amount of 0.0001 to 20 mol %, preferably 0.001 to 3 mol %, based on the compound of the formula II.

Bases which can be used in the process according to the invention are both inorganic and organic compounds which are sufficiently soluble in the reaction medium. Examples of suitable bases are compounds of the formulae V to VII $$(Z')^n \oplus (\ominus OOCQ')_n \quad (V)$$

$$\begin{array}{c} Q_5 \\ N-Q_6 \\ Q_7 \end{array} \quad (VI) \quad or \quad \begin{array}{c} Q_8 \\ \diagdown \\ N-Q-N \\ \diagup \\ Q_8 \end{array} \begin{array}{c} Q_8 \\ \diagdown \\ Q_8 \end{array} \quad (VII)$$

as well as cyclic tertiary amines, for example N-methylpiperidine, N-ethylpiperidine, 1,2,2,6,6-pentamethylpiperidine, 4-oxo-1,2,2,6,6-pentamethylpiperidine, 1,4-diazabicyclo[2.2.2]octane (DABCO), N-alkylmorpholines and N-alkylpyrrolidines, such as N-methylmorpholine, N-ethylmorpholine, N-methylpyrrolidine and N-ethylpyrrolidine, and N,N'-dialkylpiperazines, such as N,N'-dimethylpiperazine.

In the above formulae n is 1 or 2, Q' is phenyl or C$_{1-17}$-alkyl, Z' is an alkali metal cation, an alkaline earth metal cation or

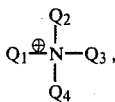

Q is straight-chain or branched alkylene having 2–6 C atoms, Q$_1$ is hydrogen, C$_{1-12}$-alkyl, cyclopentyl, cyclohexyl, benzyl or phenyl, Q$_2$, Q$_3$ and Q$_4$ are identical or different C$_{1-12}$-alkyl, Q$_5$ is C$_{1-12}$-alkyl, cyclopentyl, cyclohexyl, phenyl or benzyl, which can also be substituted, for example by a halogen atom, such as chlorine or bromine, or by an alkyl or alkoxy group having 1–4, and especially 1 or 2, C atoms, Q$_6$ and Q$_7$ are identical or different C$_{1-12}$-alkyl and Q$_8$ is methyl or ethyl.

An alkali metal cation Z' is in particular the sodium cation and very especially the lithium cation. Alkyl groups Q' and Q$_1$ to Q$_7$ can be straight-chain or branched. If Q$_5$ to Q$_7$ are alkyl groups, these advantageously conjointly have not less than 8 C atoms, whilst alkyl groups Q$_1$ to Q$_4$ preferably each have 1–4 C atoms. Examples of compounds of the formulae V to VII are lithium acetate, butyrate and stearate, barium acetate, calcium acetate, potassium stearate, calcium stearate, sodium stearate, lithium benzoate, sodium benzoate and the corresponding trimethylammonium, tetramethylammonium, tetraethylammonium and tetra-n-butylammonium salts; triethylamine, tri-n-butylamine, tri-(2-ethylhexylamine), tri-n-octylamine and tri-n-dodecylamine; N-benzyldialkylamines, such as N-benzyldimethylamine, N-benzyldiethylamine, N-(4-chlorobenzyl)-dimethylamine and N-(3-methyl- or 3-methoxybenzyl)-dimethylamine; N,N,N',N'-tetramethyl- and N,N,N',N'-tetraethyl-ethylenediamine, N,N,N',N'-tetramethyl-1,3-diaminopropane and N,N,N',N'-tetramethyl-1,6-diaminohexane.

The preferred bases are tertiary amines of the above-mentioned type, especially N-ethylmorpholine, or compounds of the formula VI, in which Q$_5$ is 4-chlorobenzyl, 3-methylbenzyl or 3-methoxybenzyl and especially benzyl and Q$_6$ and Q$_7$ are each alkyl having 1–4 C atoms, especially 1 or 2 C atoms, or in which Q$_5$, Q$_6$ and Q$_7$ are each alkyl having 3–12 C atoms. N-Benzyldimethylamine, N-ethylmorpholine and tri-n-butylamine are particularly preferred.

The reaction temperature, for the reaction according to the invention, is advantageously between 0° and 200° C., preferably between 90° and 150° C. If the acid halide of the formula II is liquid, the reaction can be carried out without addition of a solvent. However, the reaction is preferably carried out in an organic solvent which is inert towards the reactants. Examples of suitable inert organic solvents are aliphatic, cycloaliphatic or aromatic hydrocarbons and chlorohydrocarbons, such as n-pentane, n-heptane, n-octane, cyclopentane, cyclohexane, benzene, toluene, xylenes and chlorobenzene; aromatic, aliphatic and cyclic ethers, such as anisole, diethyl ether, di-isopropyl ether, tetrahydrofuran and dioxane; nitriles, especially benzonitrile and alkylnitriles having 2 to 5 C atoms, such as acetonitrile, propionitrile and butyronitrile; 3-methoxypropionitrile and 3-ethoxypropionitrile; N,N-dialkylamides of of aliphatic monocarboxylic acids having 1 to 3 C atoms in the acid moiety, such as N,N-dimethylformamide and N,N-dimethylacetamide; tertiary alcohols having 4 to 8 C atoms, especially tert.-butanol; aliphatic and cycloaliphatic ketones, such as acetone, diethyl ketone, methyl isopropyl ketone, cyclopentanone and cyclohexanone; esters, such as esters of carbonic acid, for example diethyl carbonate, and alkyl esters and alkoxyalkyl esters of aliphatic monocarboxylic acids having a total of 2 to 8 C atoms, such as methyl, ethyl, n-butyl and isobutyl acetate, ethyl and n-butyl butyrate and 1-acetoxy-2-methoxyethane. Preferred solvents are nitriles, ketones, esters, cyclic ethers and aromatic hydrocarbons of the abovementioned type. Suitable solvents for the reaction in the presence of an inorganic base are, in particular, polar solvents, such as nitriles, ketones and esters. In the most preferred case, the reaction is carried out in the presence of an organic base and of an aromatic ether or hydrocarbon, especially anisole, a xylene or toluene.

In the process according to the invention, the course of the reaction can easily be followed from the evolution of CO, for example by using a bubbler. In the case of reaction products which are of limited solubility in the reaction mixture, it is advisable to stop the reaction when the evolution of CO has ceased and to work up the reaction product directly.

The compounds which can be prepared according to the invention, and their uses, are for a large part known; for example, some of the compounds can be used directly as fluorescent brighteners or scintillators. Such fluorescent brighteners are described, for example, in British Pat. Nos. 1,247,934 and 1,445,231. Compounds suitable for use as scintillators are, for example, those of the type described in British Patent Application No. 2,015,021 [cf. also A. Dyer, "An Introduction to Liquid Scintillation Counting", Heyden Publ., London-New York, 1947, page 16]. The compounds prepared according to the invention can furthermore be converted, in a manner known per se, with or without introduction of suitable functional groups, such as amino groups, and/or with sulfonation of the aromatic radicals Z and $Z_1$, into dyes of fluorescent brighteners [cf., for example, Encyclopedia of Chemical Technology, 2nd edition, Volume 19, pages 1 to 16]. Stilbene and stilbene derivatives are also used as additives to adhesives, and as insecticides and light stabilisers, cf., for example, Chemical Abstracts 78, 39352; 84, 137,386 and 85, 22,416.

EXAMPLE 1

7.05 g (0.05 mol) of benzoyl chloride, 6.5 g (0.0625 mol) of styrene, 8.65 g (0.05 mol) of tri-n-butylamine, 0.1122 g (0.0005 mol) of palladium acetate and 100 ml of p-xylene are introduced into a 250 ml flask and heated to 120° C., with stirring. A slight evolution of gas is observed. After the mixture has been stirred for 2 hours at 120° C., it is cooled and extracted by shaking with 2×25 ml portions of 2 N hydrochloric acid, and the organic phase is dried with magnesium sulfate. The p-xylene is distilled off and the residue is recrystallised from ethanol. 8.0 g (0.0445 mol) of stilbene are obtained as a colourless, crystalline compound, corresponding to a yield of 89% of theory; melting point 125° C.

Analysis for $C_{14}H_{12}$ (molecular weight 180): calculated C, 93.29%, H, 6.71%; found C, 93.60%, H, 6.63%.

EXAMPLE 2

The procedure described in Example 1 is followed, except that 8.43 g (0.05 mol) of 4-formylbenzoyl chloride, 6.5 g (0.0625 mol) of styrene, 17.5 g (0.05 mol) of tri-n-octylamine, 100 ml of dioxane as the solvent and 0.287 g (0.0005 mol) of bis-(dibenzylideneacetone)-palladium(O) are used. After a reaction time of 2 hours at 120° C., 5.8 g (0.0279 mol) of 4-formylstilbene, corresponding to a yield of 56% of theory, are obtained as yellowish crystals; melting point 112°–113° C.

Analysis for $C_{15}H_{12}O$ (molecular weight 208): calculated C, 86.51%. H, 5.81%, O, 7.68%; found C, 85.99%, H, 6.08%, O, 7.33%.

EXAMPLE 3

The procedure described in Example 1 is followed, except that 17.5 g (0.1 mol) of 4-chlorobenzoyl chloride, 13.02 g (0.125 mol) of styrene, 35.37 g (0.1 mol) of tri-2-ethylhexylamine and 0.1773 g (0.01 mol) of palladium chloride are used. After a reaction time of 4 hours at 120° C., 9.3 g (0.0433 mol) of 4-chlorostilbene, corresponding to a yield of 43.3% of theory, are obtained in the form of white flakes; melting point 129°–130° C.

Analysis for $C_{14}H_{11}Cl$ (molecular weight 214.5): calculated C, 78.32%, H, 5.16%; found C, 78.07%, H, 5.16%.

EXAMPLE 4

The procedure described in Example 1 is followed, except that 20.3 g (0.1 mol) of terephthalic acid dichloride, 26.04 g (0.25 mol) of styrene, 53.9 g (0.25 mol) of tri-n-hexylamine and 0.5329 g (0.002 mol) of palladium nitrate dihydrate are used. After a reaction time of 3 hours at 120° C., 8.5 g (0.0301 mol) of 4,4'-distyrylbenzene, corresponding to a yield of 30.1% of theory, are obtained in the form of greenish yellow flakes; melting point 267° C., Analysis for $C_{22}H_{18}$ (molecular weight 282): calculated C, 93.58%, H, 6.43%; found C, 93.58%, H, 6.44%.

EXAMPLE 5

The procedure described in Example 1 is followed, except that 13.95 g (0.05 mol) of 4,4'-biphenyldicarboxylic acid dichloride, 13.0 g (0.125 mol) of styrene, 23.13 g (0.125 mol) of tri-n-butylamine and 0.224 g (0.001 mol) of palladium acetate are used. After a reaction time of 3 hours in 100 ml of propionitrile as the solvent, at 100° C., 5.1 g (0.0143 mol) of 4,4'- distyrylbiphenyl, corresponding to a yield of 28.6% of theory, are obtained; melting point 323°–325° C.

Analysis for $C_{28}H_{22}$ (molecular weight 358): calculated C, 93.81%, H, 6.19%; found C, 93.39%, H, 6.08%.

EXAMPLE 6

The procedure described in Example 1 is followed, except that 16.7 g (0.1 mol) of cinnamyl chloride, 13.0 g (0.125 mol) of styrene, 23.3 g (0.125 mol) of tri-n-butylamine, 100 ml of chlorobenzene and 0.225 g (0.001 mol) of palladium acetate are used. After a reaction time of 5 hours at a bath temperature of 140° C., 5.7 g (0.0277 mol) of 1,4-diphenyl-1,3-butadiene, corresponding to a yield of 27.7% of theory, are obtained; melting point 150°–152° C.

EXAMLE 7

The procedure described in Example 1 is followed, except that 19.1 g (0.1 mol) of 2-naphthoyl chloride, 13.1 g (0.125 mol) of styrene, 23.2 g (0.125 mol) of tri-n-butylamine and 0.225 g (0.001 mol) of palladium acetate are used. After a reaction time of 2 hours at 130° C., in 100 ml of ethyl butyrate, 10.2 g (0.0445 mol) of 2-styrylnaphthalene, corresponding to a yield of 44.5% of theory, are obtained; melting point 143°–145° C.

EXAMPLE 8

The procedure described in Example 1 is followed, except that 15.5 g (0.1 mol) of o-toluic acid chloride, 13 g (0.125 mol) of styrene, 23.2 g (0.125 mol) of tri-n-butylamine and 0.225 g (0.001 mol) of palladium acetate are used. After a reaction time of 4 hours at 120° C., in 100 ml of cyclohexanone as the solvent, 10.8 g (0.0556 mol) of 2-methylstilbene, corresponding to a yield of 55.6% of theory, are obtained; melting point 92°–93° C.

EXAMPLE 9

The procedure described in Example 1 is followed, except that 17.1 g (0.1 mol) of 2-methoxybenzoyl chloride, 13 g (0.125 mol) of styrene, 23.2 g (0.125 mol) of tri-n-butylamine and 0.225 g (0.001 mol) of palladium acetate are used. After a reaction time of 3 hours at a bath temperature of 140° C., in 100 ml of diethyl carbonate as the solvent, 10.3 g (0.049 mol) of 2-methoxystilbene, corresponding to a yield of 49% of theory, are obtained; melting point 69°–70° C.

EXAMPLE 10

The procedure described in Example 1 is followed, except that 26.65 g (0.1 mol) of 3-iodobenzoyl chloride, 13 g (0.125 mol) of styrene, 12.93 g (0.1 mol) of ethyldiisopropylamine and 0.575 g (0.001 mol) of bis-(dibenzylidene-acetone)-palladium(O) are used. After a reaction time of 3 hours at the reflux temperature in 150 ml of propionitrile, 3.05 g (0.01 mol) of 3-iodostilbene, corresponding to a yield of 10% of theory, are obtained; melting point 96° C.

Analysis for $C_{14}H_{11}I$ (molecular weight 216): calculated C, 54.93%, H, 3.62%, I, 41.49%; found C, 55.35%, H, 3.70%, I, 41.22%.

EXAMPLE 11

The procedure described in Example 1 is followed, except that 15.46 g (0.1 mol) of p-toluic acid chloride, 13.02 g (0.125 mol) of styrene, 14.3 g (0.1 mol) of tri-n-propylamine and 0.177 g (0.001 mol) of palladium chloride are used. After a reaction time of 3 hours at 130° C., in 50 ml of chlorobenzene as the solvent, 5.8 g (0.03 mol) of 4-methylstilbene, corresponding to a yield of 30% of theory, are obtained; melting point 117° C.

Analysis for $C_{15}H_{14}$ (molecular weight 194): calculated C, 92.74%, H, 7.26%; found C, 92.93%, H, 7.26%.

EXAMPLE 12

The procedure described in Example 1 is followed, except that 16.55 g (0.1 mol) of 4-cyanobenzoyl chloride, 13.02 g (0.125 mol) of styrene, 35.37 g (0.1 mol) of tri-n-octylamine, 50 ml of ethyl butyrate as the solvent and 0.0575 g (0.0001 mol) of bis-(dibenzylideneacetone)-palladium(O) are used. After a reaction time of 2 hours at 100° C., 5.5 g (0.0268 mol) of 4-cyanostilbene, corresponding to a yield of 26.8% of theory, are obtained; melting point 119° C.

Analysis for $C_{15}H_{11}N$ (molecular weight 205): calculated C, 87.77%, H, 5.40%, N, 6.82%; found C, 87.55%, H, 5.62%, N, 6.73%.

EXAMPLE 13

The procedure described in Example 1 is followed, except that 23.07 g (0.1 mol) of 3,4,5-trimethoxybenzoyl chloride, 13.02 g (0.125 mol) of styrene, 12.93 g (0.125 mol) of ethyl diisopropylamine and 0.3046 g (0.001 mol) of bis-(acetylacetonato)-palladium(II) are used. After a reaction time of 3 hours at 130° C., in 50 ml of cyclohexanone as the solvent, 4.7 g (0.0175 mol) of 3,4,5-trimethoxystilbene, corresponding to a yield of 17.5% of theory, are obtained in the form of white needles; melting point 108° C.

Analysis for $C_{17}H_{18}O_3$ (molecular weight 270): calculated C, 75.53%, H, 6.71%; found C, 75.54%, H, 6.61%.

EXAMPLE 14

0.112 mg (0.5 millimols) of palladium acetate, 10.97 g (50 millimols) of 4-bromobenzoyl chloride, 10.17 g (50 millimols) of 4-bromostyrene and 6.76 g (50 millimols) of N-benzyldimethylamine in 100 m of o-xylene are stirred for 1 hour at 130° C. After having filtered off the amine salt which has precipitated, the filtrate is concentrated and the crude product is recrystallised twice from toluene. 7.8 g (46% of theory) of 4,4'-dibromostilbene are obtained in the form of white flakes; melting point 213.3° C.

Analysis for $C_{14}H_{10}Br_2$: calculated C, 49.75%, H, 2.98%; found C, 49.79%, H, 3.07%.

EXAMPLE 15

0.448 g (2 millimols) of palladium acetate, 28.11 g (0.2 mol) of benzoyl chloride, 23.64 g (0.2 mol) of α-methylstyrene and 27.04 g (0.2 mol) of N-benzyldimethylamine in 400 ml of p-xylene are stirred for 11 hours at 130° C. The mixture is extracted by shaking with 400 ml of 2 NHCl and 400 ml of 2 N NaOH and is then dried over magnesium sulfate. The crude product is chromatographed on silica gel in methylene chloride and subsequently recrystallised from n-pentane. 1.3 g (3% of theory) of α-methylstilbene are obtained as colourless crystals of melting point 79.0° C.

Analysis for $C_{15}H_{14}$: calculated C, 92.74%, H, 7.27%; found C, 92.65%, H, 7.17%.

EXAMPLE 16

The procedure described in Example 14 is followed, except that 5.91 g (50 millimols) of 4-methylstyrene are used. The mixture is stirred for one hour at 130° C. The crude product is recrystallised from toluene/cyclohexane. 7.4 g (54% of theory) of 4-bromo-4'-methylstilbene are obtained as white crystals of melting point 214.6° C.

Analysis for $C_{15}H_{13}Br$: calculated C, 65.95%, H, 4.80%; found C, 65.72%, H, 4.71%.

EXAMPLE 17

The procedure described in Example 14 is followed, except that 9.64 g (50 millimols) of 1-vinylnaphthalene are used. The mixture is stirred for 3½ hours at 130° C. The crude product is chromatographed in toluene on silica gel and is then recrystallised once from n-hexane and once from n-hexane/n-pentane. 3.0 g (19% of theory) of 1-(4-bromostyryl)-naphthalene are obtained as pale yellow crystals of melting point 105.6° C.

Analysis for $C_{18}H_{13}Br$: calculated C, 69.92%, H, 4.24%; found C, 69.99%, H, 4.24%.

EXAMPLE 18

0.448 g (2 millimols) of palladium acetate, 43.88 g (0.2 mol) of 4-bromobenzoyl chloride, 26 g (0.25 mol) of styrene and 37.06 g (0.2 mol) of tri-n-butylamine in 200 mol of p-xylene are stirred for 4 hours at 120° C. After the reaction mixture has been extracted by shaking with 2 N HCl and 2 N NaOH, and dried over magnesium sulfate, the crude product is chromatographed in toluene on silica gel, and is recrystallised from n-hexane. 26.43 g (51% of theory) of 4-bromostilbene are obtained as pale yellow crystals of melting point 137.7° C.

Analysis for $C_{14}H_{11}Br$: calculated C, 64.89%, H, 4.28%; found C, 65.20%, H, 4.32%.

EXAMPLE 19

The procedure described in Example 18 is followed, except that 33.7 g (0.2 mol) of 3,4-dimethylbenzoyl chloride are used. The mixture is stirred for 2 hours at 120° C. The crude product is recrystallised once from methanol and once from n-hexane. 15.8 g (38% of theory) of 3,4-dimethylstilbene are obtained in the form of pale yellow crystals, of melting point 76° C.

Analysis for $C_{16}H_{16}$: calculated C, 92.26%, H, 7.74%; found C, 92.06%, H, 7.69%.

EXAMPLE 20

The procedure described in Example 18 is followed, except that 41.89 g (0.2 mol) of 3,4-dichlorobenzoyl chloride are used. The mixture is stirred for 1 hour at 120° C. The crude product is extracted in a Soxhlet and is recrystallised from n-pentane. 28.6 g (57% of theory) of 3,4-dichlorostilbene are obtained in the form of white flakes; melting point 87.7° C.

Analysis for $C_{14}H_{10}Cl_2$: calculated C, 67.50%, H, 4.50%, Cl, 28.46%; found C, 67.80%, H, 4.08%, Cl, 28.65%.

EXAMPLE 21

The procedure described in Example 18 is followed, except that 39.91 g (0.2 mol) of 2-methyl-5-nitrobenzoyl chloride are used. The mixture is stirred for 1.5 hours at 120° C. The crude product is extracted in a Soxhlet and is recrystallised from cyclohexane/n-hexane. 20.9 g (44% of theory) of 2-methyl-5-nitrostilbene are obtained as pale yellow crystals of melting point 65.5° C.

Analysis for $C_{15}H_{13}NO_2$: calculated C, 75.30%, H, 5.48%, N, 5.86%; found C, 75.12%, H, 5.62%, N, 5.87%.

EXAMPLE 22

The procedure described in Example 18 is followed, except that 39.91 g (0.2 mol) of 2-methyl-3-nitrobenzoyl chloride are used. The mixture is stirred for 30 minutes at 120° C. The crude product is chromatographed on silica gel in toluene and is then recrystallised from n-hexane. 28.5 g (60% of theory) of 2-methyl-3-nitrostilbene are obtained as pale yellow crystals of melting point 75.9° C.

Analysis for $C_{15}H_{13}NO_2$: calculated C, 75.30%, H, 5.48%, N, 5.86%; found C, 75.30%, H, 5.64%, N, 5.88%.

EXAMPLE 23

The procedure described in Example 18 is followed, except that 40.1 g (0.2 mol) of 3,5-dimethoxybenzoyl chloride are used. The mixture is stirred for 2.5 hours at 120° C. The crude product is chromatographed on silica gel in methylene chloride and is then recrystallised from n-hexane. 27.6 g (58% of theory) of 3,5-dimethoxystilbene are obtained as white crystals of melting point 56.4° C.

Analysis for $C_{16}H_{16}O_2$: calculated C, 79.98%, H, 6.71%; found C, 80.6%, H, 6.8%.

EXAMPLE 24

The procedure described in Example 18 is followed, except that 43.30 g (0.2 mol) of biphenyl-4-carboxylic acid chloride are used. The mixture is stirred for 3 hours at 120° C. The crude product is filtered off and recrystallised from toluene. 28.5 g (56% of theory) of 4-phenylstilbene are obtained as pale yellow crystals of melting point 223.7° C.

Analysis for $C_{20}H_{16}$: calculated C, 93.71%, H, 6.29%; found C, 93.61%, H, 6.24%.

EXAMPLE 25

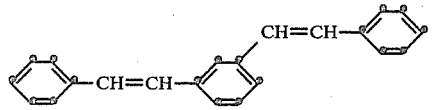

0.896 g (4 millimols) of palladium acetate, 40.6 g (0.2 mol) of isophthalic acid dichloride, 52.0 g (0.5 mol) of styrene and 74.12 g (0.4 mol) of tri-n-butylamine in 300 ml of p-xylene are stirred for 2¾ hours at 120° C. The crude product is extracted in a Soxhlet and is recrystallised from n-hexane/cyclohexane. 14.0 g (25% of theory) of the above compound are obtained in the form of white crystals, of melting point 173.0° C.

Analysis for $C_{22}H_{18}$: calculated C, 93.58%, H, 6.45%; found C, 93.51%, H, 6.77%.

EXAMPLE 26

0.224 g (1 millimol) of palladium acetate, 12.65 g (50 millimols) of naphthalene-2,6-dicarboxylic acid dichloride, 13.04 g (125 millimols) of styrene and 18.53 g (100 millimols) of tri-n-butylamine in 50 ml of p-xylene are stirred for 2 hours at 120° C. The crude product is extracted in a Soxhlet and recrystallised from tetrahydrofuran. 6.1 g (37% of theory) of 2,6-distyrylnaphthalene are obtained as pale yellow crystals of melting point 294.7° C.

Analysis for $C_{26}H_{20}$: calculated C, 93.93%, H, 6.07%; found C, 93.73%, H, 6.24%.

EXAMPLE 27

The procedure described in Example 26 is followed, except that 12.65 g (50 millimols) of naphthalene-1,4-dicarboxylic acid dichloride are used. The mixture is stirred for 2 hours at 120° C. The crude product is chromatographed on silica gel in methylene chloride and is then recrystallised from cyclohexane. 10.6 g (64% of theory) of 1,4-distyrylnaphthalene are obtained as yellow crystals of melting point 189° C.

Analysis for $C_{26}H_{20}$: calculated C, 93.93%, H, 6.07%; found C, 93.40%, H, 6.10%.

EXAMPLE 28

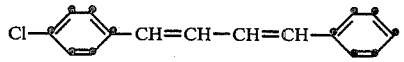

(1-Phenyl-4-(4'-chlorophenyl)-buta-1,3-diene)

0.112 g (0.5 millimol) of palladium acetate, 10.05 g (50 millimols) of 4-chlorocinnamyl chloride, 6.5 g (62.5 millimols) of styrene and 9.27 g (50 millimols) of tri-n-butylamine in 50 ml of p-xylene are stirred for 2¾ hours at 120° C. The crude product is chromatographed on silica gel in methylene chloride and is recrystallised from n-hexane. 0.5 g (4% of theory) of the above compound are obtained in the form of white crystals of melting point 161.2° C.

Analysis for $C_{16}H_{13}Cl$: calculated C, 79.83%, H, 5.45%, Cl, 14.73%; found C, 79.63%, H, 5.35%, Cl, 14.79%.

EXAMPLE 29

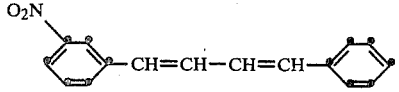

(1-Phenyl-4-(3'-nitrophenyl)-buta-1,3-diene)

The procedure described in Example 28 is followed, except that 10.58 g (50 millimols) of 3-nitrocinnamyl chloride are used. The mixture is stirred for 3 hours at 120° C. The crude product is chromatographed on silica gel in toluene and recrystallised from cyclohexane. 0.8 g (6% of theory) of the above compound are obtained as yellow crystals of melting point 143.9° C.

Analysis for $C_{16}H_{13}NO_2$: calculated C, 76.48%, H, 5.22%, N, 5.58%; found C, 76.49%, H, 5.19%, N, 5.59%.

EXAMPLE 30

0.095 g (0.25 millimol) of diacetatobipyridyl-palladium(II), 3.52 g (25 millimols) of benzoyl chloride, 2.61 g (25 millimols) of styrene and 3.38 g (25 millimols) of N-benzyldimethylamine in 50 ml of p-xylene are stirred for 100 minutes at 130° C. After working up the mixture as described in the preceding examples, 2.71 g (52% of theory) of stilbene are obtained.

EXAMPLE 31

1.12 ml (0.005 millimol) of palladium acetate, 7.04 g (50 millimols) of benzoyl chloride, 5.22 g (50 millimols) of styrene and 6.76 g (50 millimols) of N-benzyldimethylamine in 100 ml of p-xylene are stirred for 11.5 hours at 130° C. 6.54 g (63% of theory) of stilbene are obtained. This corresponds to 6,300 mols of stilbene per mol of catalyst.

EXAMPLE 32

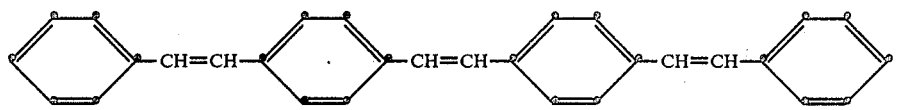

0.1122 g (0.0005 mol) of palladium acetate are dissolved in 100 ml of o-xylene; 7.63 g (0.025 mol) of stilbene-4,4'-dicarboxylic acid dichloride, 5.75 ml (0.050 mol) of styrene and 7.53 ml (0.050 mol) of N-benzyldimethylamine are then added successively. After a reaction time of 1.5 hours at 130° C., followed by working up, 1.6 g of stilbene-4,4'-distyryl are obtained, corresponding to a yield of 17% of theory; melting point >300° C.

Analysis for $C_{30}H_{24}$: calculated C, 93.71%, H, 6.29%; found C, 93.36%, H, 6.45%.

EXAMPLE 33

Using various catalysts and the procedure described in the preceding examples, trans-stilbene is prepared as follows: 0.25 millimol of one of the catalysts listed below, 2.89 ml (25 millimols) of benzoyl chloride, 2.88 ml (25 millimols) of styrene and 3.77 ml (25 millimols) of N-benzyldimethylamine are added to 50 ml of p-xylene under argon and the reaction mixture is stirred for 1–3 hours at 130° C. After working up the mixture, trans-stilbene is obtained in the yields shown below:

| Catalyst | Yield |
|---|---|
| 0.08 g (0.25 millimol) of bis-(cyclohexyl-isonitrile)-palladium(0), 2 hpurs' stirring | 70% of theory |
| 0.0833 g (0.25 millimol) of PdCl$_2$[OS(CH$_3$)$_2$]$_2$, 2 hours' stirring | 15% of theory |
| 0.0958 g (0.25 millimol) of PdCl$_2$(NC-phenyl)$_2$, 1 hour' stirring | 74% of theory |
| 0.0951 g (0.25 millimol) of Pd(OOCCH$_3$)$_2$(2,2'-bipyridyl), 3 hourrs' stirring | 69% of theory |

EXAMPLE 34

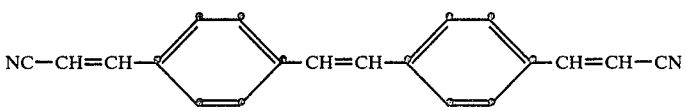

0.68 g (4.44 millimols) of 4-vinylcinnamonitrile, 0.85 g (4.44 millimols) of cinnamonitrile-4-carboxylic acid chloride and 0.60 g (4.44 millimols) of N-benzyldimethylamine are added to a solution of 9.85 mg (0.044 millimol) of palladium acetate in 19.7 ml of p-xylene, under argon. The mixture is stirred for 4 hours at 130° C., cooled to room temperature and filtered. The precipitate is rinsed with methanol and is then dissolved in 20 ml of hot N,N-dimethylformamide, 10 ml of water are added and the mixture is cooled to 0° C. 0.62 g (50% of theory) of the above fluorescent brightener is obtained; melting point 220° C.

4-Vinylcinnamonitrile, used as the starting material, is a novel compound and is also a subject of the invention. It can be prepared as follows: 2.08 g (10 millimols) of 4-bromocinnamonitrile, 1.85 g (10 millimols) of tri-n-butylamine, 0.0224 g (0.1 millimol) of palladium acetate and 0.0608 g (0.2 millimol) of tri-o-tolylphosphine are added to 6 ml of p-xylene and 6 mg of hydroquinone monomethyl ester, under argon. The mixture is then stirred for 4 hours at 10 bar under ethylene. Thereafter it is filtered at room temperature and extracted by shaking with 40 ml of 2 N HCl and 40 ml of 2 N NaOH. After drying the mixture over magnesium sulfate, and concentrating it, the crude product is twice recrystallised from n-pentane. 0.22 g (14% of theory) of 4-vinylcinnamonitrile is obtained in the form of white crystals; melting point 45.8° C.

Analysis for $C_{11}H_9N$: calculated C, 85.13%, H, 5.85%, N, 9.02%; found C, 84.6%, H, 5.9%, N, 9.0%.

EXAMPLE 35

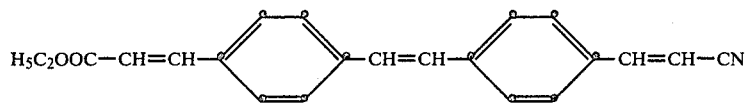

0.84 g (5.49 millimols) of 4-vinylcinnamonitrile, 1.309 g (5.49 millimols) of ethyl cinnamate-4-carboxylic acid chloride and 0.742 g (5.49 millimols) of N-benzyldimethylamine are added to 12.25 mg (0.0549 millimol) of palladium acetate in 24.5 ml of p-xylene, under argon. The mixture is stirred for 5.5 hours at 130° C. It is then diluted with 100 ml of toluene and extracted by shaking with 100 ml of 2 N HCl and 100 ml of 2 N NaOH. After having been dried with magnesium sulfate, the solution is evaporated and the crude product is recrystallised once from 100 ml of carbon tetrachloride and once from 50 ml of ethanol. 0.47 g (26% of theory) of the above optical brightener are obtained in the form of pale yellow crystals; melting point 155.1° C.

Analysis for $C_{20}H_{14}N_2$: calculated C, 80.22%, H, 5.82%, N, 4.25%; found C, 80.17%, H, 5.79%, N, 4.20%.

EXAMPLE 36

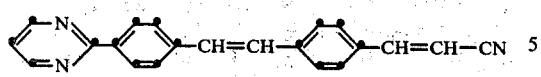

0.449 g (0.2 millimol) of palladium acetate, 0.1048 g (0.4 millimol) of triphenylphosphine, 4.7 g (20 millimols) of 2-(4-bromophenyl)-pyrimidine [prepared by reacting 4-bromobenzamidine with malonodialdehyde in a basic medium], 3.1 g (20 millimols) of 4-vinylcinnamonitrile and 4.47 g (20 millimols) of tri-n-butylamine are added to 20 ml of p-xylene under argon and the mixture is stirred for 6 hours at 130° C. The resulting crude product is filtered off at room temperature and is twice recrystallised from toluene/carbon tetrachloride. 1.9 g (31% of theory) of the above compound are obtained in the form of yellow crystals; melting point 290°–291° C.

Analysis for $C_{21}H_{15}N_3$: calculated C, 81.32%, H, 4.87%, N, 13.46%; found C, 81.55%, H, 4.85%, N, 13.59%.

What is claimed is:

1. A process for the preparation of a compound of the formula I

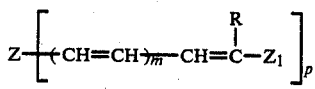     (I)

in which, if p=1, Z is substituted or unsubstituted phenyl or naphthyl and, if p=2, Z is substituted or unsubstituted phenylene, naphthylene or p-biphenylene, $Z_1$ is substituted or unsubstituted phenyl or naphthyl, R is hydrogen or $C_{1-4}$-alkyl, m is zero or 1 and p is 1 or 2, wherein a compound of the formula II

     (II)

in which Z, m and p are as defined under formula I and X is chlorine, bromine or iodine, is reacted, in the presence of a base and with the addition, as a catalyst, of palladium metal or of a palladium compound which under the reaction conditions forms a phosphorus-free labile palladium-(O) compound, with a compound of the formula III or, if p=2, alternatively with a mixture of two different compounds of the formula III

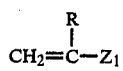     (III)

in which R and $Z_1$ are as defined under formula I.

2. A process according to claim 1, wherein a compound of the formula II, in which X is chlorine, is used.

3. A process according to claim 1, wherein the acid halide used is isophthalic acid dichloride, terephthalic acid dichloride, 1,4- or 2,6-naphthalenedicarboxylic acid dichloride, 4,4'-diphenyldicarboxylic acid dichloride or a compound of one of the formulae IIa, IIb, IIc or IIg

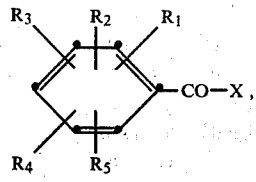     (IIa)

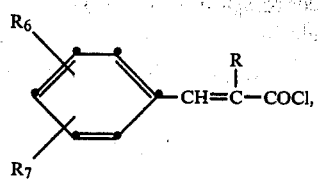     (IIb)

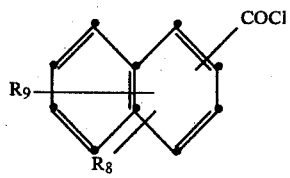     (IIc)

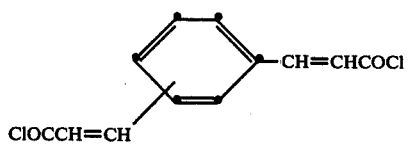     (IIg)

in which X is chlorine, $R_1$ is hydrogen, formyl, methyl, methoxy, cyano, nitro, Cl, Br, F, I, —CH═CHCN, —CH═CHCOOCH$_3$, —CH═CHCOOC$_2$H$_5$ or phenyl, $R_2$ is hydrogen, methyl, methoxy, Cl or Br, $R_3$ is hydrogen or methoxy, $R_4$ and $R_5$ are hydrogen, R is methyl or, especially, hydrogen, $R_6$ is hydrogen, Cl or nitro, $R_7$ is hydrogen, $R_8$ is methyl or, especially, hydrogen and $R_9$ is hydrogen, and the —CH═CHCOCl groups are in the 1,3- or 1,4-position and the —COCl group in formula IIc is in the 1- or 2-position.

4. A process according to claim 1, wherein the palladium compound used is PdCl$_2$, PdBr$_2$, Pd(OOCCH$_3$)$_2$,

Pd(OOCCH$_3$)$_2$(2,2'-bipyridyl), PdCl$_2$(NC-phenyl)$_2$, bis-(dibenzylidene-acetone)-palladium(O) or bis-(cyclohexylisonitrile)-palladium(O).

5. A process according to claim 1, wherein the palladium compound used is PdCl$_2$, palladium acetate or bis-(dibenzylidene-acetone)-palladium(O).

6. A process according to claim 1, wherein the reaction is carried out at a temperature of between 0° and 200° C. and in the presence of an organic solvent which is inert towards the reactants.

7. A process according to claim 6, wherein the solvent used is anisole, a xylene or toluene.

8. A process according to claim 1, wherein the base used is a compound of the formula VI

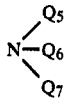     (VI)

in which $Q_5$ is 4-chlorobenzyl, 3-methylbenzyl, 3-methoxybenzyl or benzyl and $Q_6$ and $Q_7$ are each alkyl having 1-4 C atoms, or wherein $Q_5$, $Q_6$ and $Q_7$ are each alkyl having 3-12 C atoms.

9. A process according to claim 1, wherein the base used is N-benzyldimethylamine, N-ethylmorpholine or tri-n-butylamine.

10. A process according to claim 1, wherein a compound of the formula III, in which R is methyl or, especially, hydrogen, and $Z_1$ is chlorophenyl, bromophenyl, cinnamonitrile, methylphenyl, methoxyphenyl, naphthyl or, especially, phenyl, is used.

11. A process according to claim 1, wherein the catalyst is used in an amount of 0.001 to 3 mol %, based on the compound of the formula II.

12. A process according to claim 1, wherein 4-bromobenzoyl chloride or benzoyl chloride is used as the compound of the formula II and 4-bromostyrene or styrene as the compound of the formula III.

13. 4-Vinylcinnamonitrile.